United States Patent
Yagyu et al.

(10) Patent No.: US 10,258,660 B2
(45) Date of Patent: Apr. 16, 2019

(54) OLIVE LEAF EXTRACT AND METHOD OF PRODUCING THE SAME

(71) Applicant: SHODOSHIMA HEALTHYLAND CO., LTD., Shozu-gun, Kagawa (JP)

(72) Inventors: Toshihiro Yagyu, Shozu-gun (JP); Norihito Kishimoto, Shozu-gun (JP)

(73) Assignee: SHODOSHIMA HEALTHYLAND CO., LTD., Kagawa (JP)

( * ) Notice: Subject to any disclaimer, the term of this patent is extended or adjusted under 35 U.S.C. 154(b) by 0 days.

(21) Appl. No.: 15/745,520

(22) PCT Filed: Sep. 29, 2016

(86) PCT No.: PCT/JP2016/078955
§ 371 (c)(1),
(2) Date: Jan. 17, 2018

(87) PCT Pub. No.: WO2017/057647
PCT Pub. Date: Apr. 6, 2017

(65) Prior Publication Data
US 2018/0169170 A1    Jun. 21, 2018

(30) Foreign Application Priority Data

Oct. 1, 2015 (JP) .................................. 2015-195514

(51) Int. Cl.
| | | |
|---|---|---|
| *A61K 36/63* | (2006.01) | |
| *A23L 33/105* | (2016.01) | |
| *A61K 8/97* | (2017.01) | |
| *A61K 36/87* | (2006.01) | |
| *B01D 11/02* | (2006.01) | |
| *B01F 3/20* | (2006.01) | |
| *A61Q 19/00* | (2006.01) | |

(52) U.S. Cl.
CPC ............ *A61K 36/63* (2013.01); *A23L 33/105* (2016.08); *A61K 8/97* (2013.01); *A61K 36/87* (2013.01); *A61Q 19/00* (2013.01); *B01D 11/02* (2013.01); *B01F 3/2071* (2013.01)

(58) Field of Classification Search
None
See application file for complete search history.

(56) References Cited

U.S. PATENT DOCUMENTS

| | | | | |
|---|---|---|---|---|
| 8,084,067 B2 * | 12/2011 | Giori et al. | ............ | A61K 36/63 424/769 |
| 8,372,445 B2 * | 2/2013 | Giori et al. | ............ | A61K 36/87 424/725 |
| 2012/0045406 A1 | 2/2012 | Urban et al. | | |
| 2016/0030500 A1 | 2/2016 | Giuliani et al. | | |

FOREIGN PATENT DOCUMENTS

| | | |
|---|---|---|
| EP | 1 790 234 A1 | 5/2007 |
| JP | 2002-128678 A | 5/2002 |
| JP | 2003-210137 A | 7/2003 |
| JP | 2003-335693 A | 11/2003 |
| JP | 2008-201715 A | 9/2008 |
| JP | 2011-125301 A | 6/2011 |
| JP | 2012-517824 A | 8/2012 |
| KR | 101 049 776 B1 | 7/2011 |
| WO | 2014/140312 A1 | 9/2014 |

OTHER PUBLICATIONS

Dec. 6, 2016 Search Report issued in International Patent Application No. PCT/JP2016/078955.
Dec. 6, 2018 extended European Search Report issued in European Application No. 16851818.1.

* cited by examiner

*Primary Examiner* — Michael Barker
(74) *Attorney, Agent, or Firm* — Oliff PLC

(57) ABSTRACT

The present invention provides a method of producing an olive leaf extract that contains a high concentration of oleuropein. A method of producing an olive leaf extract comprises a first step of grinding dried olive leaves and a second step of mixing grapes with the ground olive leaves and then extracting an olive leaf extract using an extraction solvent. In the second step, the extraction solvent is water, alcohol, or a combination thereof, and extraction is performed at 70° C. or higher.

7 Claims, No Drawings

OLIVE LEAF EXTRACT AND METHOD OF PRODUCING THE SAME

TECHNICAL FIELD

The present invention relates to an olive leaf extract that is derived mainly from olive leaves, contains a high concentration of oleuropein, and has excellent functionality, and a method of producing the same.

BACKGROUND ART

Olive leaves have been known to have a vitamin A content much higher than the olive fruit and be rich in vitamin E as an antioxidant as well as chlorophyll and others having an anti-inflammatory action and deodorant and antibacterial actions.

It is also known that since excellent components such as vitamin A, vitamin E, and chlorophyll contained in olive leaves are efficiently incorporated in the extracted oil obtained by grinding the olive fruit and olive leaves together for extraction, the extracted oil includes a large amount of excellent components such as vitamin A, vitamin E, and chlorophyll in a natural form, compared with olive oil extract derived only from the olive fruit.

The olive fruit and leaves contain polyphenols, and their health enhancing actions have also drawn attention nowadays. Oleuropein, which is a kind of polyphenols contained in olive leaves, particularly has a very high antioxidant potency, and the effect of preventing and ameliorating various diseases have been noted.

As an example of the use of such olive leaves, Patent Document 1 discloses a method of producing an olive leaf extract including oleuropein by drying and grinding olive leaves, followed by extraction using water, water containing citric acid, or water containing peptide as an extraction solvent.

PRIOR ART DOCUMENTS

Patent Document

Patent Document 1: Japanese Patent Application Publication No. 2011-125301 (JP 2011-125301 A)

SUMMARY OF THE INVENTION

Problem to be Solved by the Invention

Unfortunately, the method disclosed in Patent Document 1 focuses on reduction in astringency and bitterness and does not disclose the optimums including extraction conditions in view of how to extract a high concentration of oleuropein.

The present invention is made in view of such a problem and an object of the present invention is to provide a method of producing an olive leaf extract containing a high concentration of oleuropein.

Means for Solving the Problem

In order to solve the problem above, a method of producing an olive leaf extract according to the present invention comprises a first step of grinding dried olive leaves and a second step of mixing grapes with the ground olive leaves and then extracting an olive leaf extract using an extraction solvent. In the second step, the extraction solvent is water, alcohol, or a combination thereof, and extraction is performed at 70° C. or higher.

In the method of producing an olive leaf extract according to the present invention, the amount of the olive leaves added with respect to the extraction solvent may be not less than 15% and not more than 35% by weight.

In the method of producing an olive leaf extract according to the present invention, the cultivar of the olive leaves may be at least one selected from the group consisting of Lucca, Mission, Nevadillo Blanco, and Manzanillo.

The present invention also provides an olive leaf extract produced by the method of producing an olive leaf extract as described above.

Effects of the Invention

The present invention can provide an olive leaf extract containing a high concentration of oleuropein and a method of producing the same.

MODES FOR CARRYING OUT THE INVENTION

The present invention provides a method of producing an olive leaf extract. The olive leaf extract is an extract derived from olive leaves and contains polyphenols such as oleuropein and hydroxytyrosol. Oleuropein and hydroxytyrosol are known as phenolic compounds having antioxidant potency, and their effects of preventing and ameliorating diseases because of the antioxidant potency have been confirmed.

The method of producing an olive leaf extract according to the present invention comprises a first step of grinding dried olive leaves and a second step of extracting an olive leaf extract from the ground olive leaves using an extraction solvent.

The first step is a step of grinding dried olive leaves. In the present description, "grinding" refers to physically crushing an object to reduce the size of the object, for example, physically crushing an object into fine particles, small pieces, powder, or the like. The method of drying olive leaves and the method of grinding olive leaves are not limited to particular methods, and any method can be used.

Examples of the cultivars of olive leaves that may be used in the present invention include Lucca, Mission, Nevadillo Blanco, Manzanillo, Amellenque, Arbequina, Ascolana Terena, Ascolano, Azapa, Barnea, Barouni, Biancolilla, Bidh El Hamman, Blanqueta, Caillet Blanc, Carolea, Cayonne, Chemilali, Chitoni, Cipressino, Coratina, Cornicabra, Correggiola, Cucco, Gigante di Cerignola, Frantoio, Glappolo, Gordal, Hardy's Mammoth, Hojiblanca, Itrana, Jumbo Kalamata, Kalamata, Koroneiki, Leccino, Leccio del Corno, Liani, Lucques, Manzanilla, Maurino, Michellenque, Moraiolo, Nabali Mohassan, Nab Tamri, Negral, Nocellara del Belice, Obliza, Oblonga, Paragon, Pendolino, Picual, Redding picholine, Redounan, Saurin large leaf, Saurin medium leaf, Saurin small leaf, Sevillano, Sorani, South Australian Verdale, St. Catherin, Taggiasca, Tanche, Tiny Oil Kalamata, Tsunati, Verdale, Wagga Verdale, Zarza, Oliviere, and FS17. In the present invention, the cultivars of olive leaves may be used singly or in combination of two or more.

The picking seasons for olive leaves are preferably, for example, but not limited to, the times around December when the olive fruit contains a high oil content in regions such as Japan in the Northern Hemisphere, or preferably the times after the olive fruit is fully ripe and harvested.

The second step is a step of extracting an olive leaf extract from the ground olive leaves using an extraction solvent.

The extraction solvent is water, alcohol, or a combination thereof. That is, the extraction solvent is water, alcohol, or water including alcohol. In the present invention, examples of the alcohol include methanol, ethanol, isopropyl alcohol, butanol, glycerol, ethylene glycol, propylene glycol, 1,3-butylene glycol, and polyethylene glycol. The alcohol may be alcohol beverages such as sake and shochu (distilled spirit). Alcohols may be used singly or in combination of two or more. The extraction solvent may be, for example, water, ethanol or 1,3-butylene glycol, or a combination thereof.

In the second step, the extraction temperature is 70° C. or higher. The extraction at 70° C. or higher yields an olive leaf extract with a high oleuropein content, as illustrated in Examples later. The upper limit of the extraction temperature is, for example, but not limited to, 100° C. or lower.

The amount of olive leaves added with respect to the extraction solvent is, but not limited to, not less than 15% by weight and not more than 35% by weight to obtain an olive leaf extract with a high oleuropein content and a high anti-glycation potency, as illustrated in Examples later.

In the second step, extraction may be performed using an extraction solvent after fruits are mixed with the ground olive leaves. Fruit itself may be used as the fruits, or fruit skin, flesh, juice, crushed product, squeezed juice, residue, or a combination thereof may be used.

In the present invention, examples of the fruits include grapes, oranges, tangerines, mandarins, grapefruits, lemons, limes, apples, peaches, strawberries, blueberries, cranberries, elderberries, bilberries, blackberries, raspberries, bananas, mangos, kiwis, pomegranates, persimmons, tomatoes, pears, cherries, plums, pineapples, loquats, and quinces. The fruits are preferably grapes. The grapes include, for example, red grapes, white grapes, and black grapes. In the present invention, fruits may be used singly or in combination of two or more.

By mixing the fruits with the olive leaves, an olive leaf extract can be extracted that contains polyphenols exceeding the sum of the theoretical value of polyphenols simply extracted from the olive leaves and the theoretical value of polyphenols extracted from the fruits. The fruits are mixed with the olive leaves to acidify water or the like as the extraction solvent in the extraction process, which presumably increases the polyphenol concentration in the obtained extract.

The present invention also provides an olive leaf extract produced by the method of producing an olive leaf extract described above. The olive leaf extract according to the present invention is produced by the method of producing an olive leaf extract according to the present invention to contain a higher concentration of oleuropein compared with conventional ones. The olive leaf extract according to the present invention thus has a high antioxidant potency and can be used in a variety of medicines, foods, and cosmetics using this antioxidant potency. In addition, the olive leaf extract according to the present invention can be used as an anti-glycation agent because of its high anti-glycation potency.

Examples (Measurement Method)

In measuring the total polyphenol content, the Folin-Ciocalteu method was used. This method uses the Folin's phenol reagent, which is reduced by phenolic hydroxy group to change color. In measuring the oleuropein content, HPLC analysis was conducted. This is called high-performance liquid chromatography and is a process for separating a certain substance in a system including a stationary phase and a mobile phase.

In measuring the anti-glycation potency, the samples were reacted with a BSA-fructose solution to produce AGEs (Advanced Glycation End Products) solution, and the amount of AGEs in the AGEs solution was measured through the competitive method.

Furthermore, in measuring the antioxidant potency, ORAC (Oxygen Radical Absorbance Capacity) was determined (reference: Wu, X. et al., J. Agric. Food Chem., m 2004, 52, 4026-4037. The activity exhibited by 1 μmol of Trolox was used as a unit).

(Olive Leaf and Extraction Solvent)

Tables 1 to 3 list the polyphenol concentration and the like of the olive leaf extracts produced through extraction from olive raw leaves, steamed leaves, and dried leaves with water, a 1,3-butylene glycol solution, or an ethanol solution. Leaves ground after drying were used as the dried leaves. The cultivar of the olive leaves used here was Mission, the extraction temperature was 50° C.-60° C., the extraction time was 5 hours, and the amount of leaves added was 10% by weight with respect to the extraction solvent. Then, the total polyphenol content (mg/100 g), the oleuropein content (mg/100 g), and the anti-glycation potency (IC50) of the olive leaf extract produced through extraction using each of water, 30% BG (BG is butylene glycol), 50% BG, 80% BG 50% EtOH (EtOH is ethanol), and 100% EtOH were measured.

TABLE 1

| Use of raw leaves | Total polyphenol content (mg/100 g) | Oleuropein content (mg/100 g) | Anti-glycation potency (IC50) |
|---|---|---|---|
| Water | 127 | 20 | 0 |
| 30% BG | 239 | 25 | 0 |
| 50% BG | 216 | 25 | 0 |
| 80% BG | 207 | 26 | 0 |
| 50% EtOH | 257 | 29 | 20 |
| 100% EtOH | 163 | 27 | 11 |

TABLE 2

| Use of steamed leaves | Total polyphenol content (mg/100 g) | Oleuropein content (mg/100 g) | Anti-glycation potency (IC50) |
|---|---|---|---|
| Water | 190 | 29 | 14 |
| 30% BG | 307 | 109 | 26 |
| 50% BG | 279 | 59 | 27 |
| 80% BG | 259 | 59 | 13 |
| 50% EtOH | 347 | 109 | 30 |
| 100% EtOH | 243 | 99 | 18 |

TABLE 3

| Use of dried leaves | Total polyphenol content (mg/100 g) | Oleuropein content (mg/100 g) | Anti-glycation potency (IC50) |
|---|---|---|---|
| Water | 248 | 39 | 26 |
| 30% BG | 378 | 46 | 33 |
| 50% BG | 414 | 238 | 29 |
| 80% BG | 423 | 329 | 30 |

TABLE 3-continued

| Use of dried leaves | Total polyphenol content (mg/100 g) | Oleuropein content (mg/100 g) | Anti-glycation potency (IC50) |
|---|---|---|---|
| 50% EtOH | 502 | 314 | 33 |
| 100% EtOH | 339 | 292 | 21 |

As listed in Tables 1 to 3, it was found that all of the total polyphenol content, the oleuropein content, and the anti-glycation potency are high when the olive leaf extract is obtained from dried leaves, compared with raw leaves and steamed leaves. When the extractions using water, water containing 1,3-butylene glycol, water containing ethanol, and 100% ethanol as an extraction solvent from the olive leaves ground after drying were compared, it was found that a sufficient total polyphenol content, a sufficient oleuropein content, and a sufficient anti-glycation potency can be obtained even using water as an extraction solvent.

(Cultivars of Olive Leaves)

Table 4 lists the polyphenol concentration and the like of the olive leaf extracts produced through extraction with water from various cultivars of olive leaves ground after drying. The cultivars of olive leaves used here were Mission, Lucca, Nevadillo Blanco, and Manzanillo. With the basic extraction conditions: the extraction temperature of 50° C. to 60° C.; the extraction time of 5 hours; and the amount of leaves added 10% by weight with respect to the extraction solvent, the total polyphenol content (mg/100 g), the oleuropein content (mg/100 g), and the anti-glycation potency (IC50) of the olive leaf extracts produced from various cultivars of olive leaves were measured.

TABLE 4

| Olive cultivar | Total polyphenol content (mg/100 g) | Oleuropein content (mg/100 g) | Anti-glycation potency (IC50) |
|---|---|---|---|
| Mission | 248 | 39 | 26 |
| Lucca | 471 | 548 | 30 |
| Nevadillo Blanco | 381 | 289 | 34 |
| Manzanillo | 423 | 330 | 41 |

When the polyphenol concentration and the like for various cultivars were measured in this manner, a favorable result was obtained for all of Lucca, Mission, Nevadillo Blanco, and Manzanillo. In particular, the most favorable values were obtained for Lucca. The olive leaves may be selected in view of cost effectiveness.

(Extraction Temperature)

Table 5 lists the polyphenol concentration and the like of the olive leaf extracts produced through extraction with water at various temperatures from olive leaves ground after drying. The cultivar of olive leaves used here was Mission, the extraction solvent was water, the extraction temperature was changed stepwise in the range from 30° C. to 100° C., the extraction time was 5 hours, and the amount of leaves added was 10% by weight with respect to the extraction solvent. Then, the total polyphenol content (mg/100 g), the oleuropein content (mg/100 g), and the anti-glycation potency (IC50) of the olive leaf extracts produced through extraction at various extraction temperatures were measured.

TABLE 5

| Extraction temperature | Total polyphenol content (mg/100 g) | Oleuropein content (mg/100 g) | Anti-glycation potency (IC50) |
|---|---|---|---|
| 30° C.-40° C. | 221 | 17 | 24 |
| 40° C.-50° C. | 223 | 18 | 28 |
| 50° C.-60° C. | 248 | 39 | 26 |
| 60° C.-70° C. | 306 | 58 | 32 |
| 70° C.-80° C. | 380 | 405 | 28 |
| 80° C.-90° C. | 408 | 489 | 30 |
| 90° C. 100° C. | 342 | 312 | 31 |

When the polyphenol concentrations of the olive leaf extracts extracted at various temperatures were compared in this manner, it was found that the oleuropein content noticeably increases at temperatures exceeding 70° C. It can therefore be said that 70° C. or higher is the optimum condition as the extraction temperature.

(Extraction Time)

Table 6 lists the polyphenol concentration and the like of the olive leaf extracts produced through extraction with water from olive leaves ground after drying for various extraction times. The cultivar of olive leaves used here was Mission, the extraction solvent was water, the extraction temperature was from 50° C. to 60° C., the extraction time was changed stepwise from 0.5 hour to 12 hours, and the amount of leaves added was 10% by weight with respect to the extraction solvent. Then, the total polyphenol content (mg/100 g), the oleuropein content (mg/100 g), and the anti-glycation potency (IC50) of the olive leaf extract produced through extraction with various extraction times were measured.

TABLE 6

| Extraction time | Total polyphenol content (mg/100 g) | Oleuropein content (mg/100 g) | Anti-glycation potency (IC50) |
|---|---|---|---|
| 0.5 hour | 235 | ND | 16 |
| 1 hour | 243 | 84 | 13 |
| 2 hours | 242 | 42 | 15 |
| 3 hours | 262 | 32 | 27 |
| 5 hours | 248 | 39 | 26 |
| 7 hours | 274 | 36 | 27 |
| 12 hours | 253 | 37 | 22 |

When the polyphenol concentrations and the like of the olive leaf extracts extracted with the extraction time changed stepwise, such as 0.5 hour, 1 hour, 2 hours, 3 hours, 5 hours, 7 hours, and 12 hours were compared in this manner, it was found that any extraction time equal to or longer than 1 hour yields a favorable result in respect of the total polyphenol, the oleuropein content, and the anti-glycation potency.

(Amount of Olive Leaf Added)

Table 7 lists the polyphenol concentration and the like of the olive leaf extracts produced through extraction with water from various added amounts (%) of olive leaves ground after drying. The cultivar of olive leaves used here was Mission, the extraction solvent was water, the extraction temperature was from 50° C. to 60° C., the extraction time was 5 hours, and the amount of leaves added was changed stepwise with respect to the extraction solvent. The total polyphenol content (mg/100 g), the oleuropein content (mg/100 g), and the anti-glycation potency (IC50) of the olive leaf extracts produced through extraction from various amounts of leaves added were measured. In conversion into the amount of raw leaves, given that the weight is reduced to 50% to 55% in the drying process, the dried leaf weight is considered as the raw leaf×0.5 to 0.55.

TABLE 7

| Amount of leaves added* | Total polyphenol content (mg/100 g) | Oleuropein content (mg/100 g) | Anti-glycation potency (IC50) |
| --- | --- | --- | --- |
| 5% | 133 | 89 | ND |
| 10% | 248 | 39 | 26 |
| 20% | 493 | 279 | 29 |
| 30% | 685 | 318 | 58 |
| 40% | 735 | 53 | 52 |

It was confirmed that the total amount of polyphenols significantly increases as the amount of olive leaves added increases. Then it was proven that when the amount of leaves added is 20% by weight, the rate of increase of the oleuropein content is extremely high compared with when the amount of leaves added is 10% by weight. It was also found that when the amount of leaves added is 20% by weight to 30% by weight, a favorable result can be obtained in respect of the oleuropein content and the anti-glycation potency. It can therefore be said that not less than 15% by weight to not more than 35% by weight is the optimum condition for the amount of leaves added.

Based on the foregoing, in the method of producing an olive leaf extract according to the present invention, the optimum conditions for obtaining an extract that contains a high concentration of polyphenols and also achieves sufficient effects in respect of the anti-glycation potency are as follows.

First Condition: Extraction Solvent

Water, alcohol, and a combination thereof can be used as the extraction solvent. For example, water, 1,3-butylene glycol, ethanol, and any combination thereof can be used. Even when water is used, a sufficient total polyphenol content, a sufficient oleuropein content, and a sufficient anti-glycation potency can be obtained.

Second Condition: Cultivar of Olive Leaves

At least Lucca, Mission, Nevadillo Blanco, or Manzanillo can be used as the olive cultivar, although not limited thereto. In particular, Lucca is most suitable in view of a high concentration of the polyphenol content.

Third Condition: Extraction Temperature

It is found that the oleuropein content significantly increases at the extraction temperature exceeding 70° C., and 70° C. or higher is most suitable.

Fourth Condition: Extraction Time

When the extraction time is, but not limited to, 1 hour or longer, a sufficient total polyphenol content, a sufficient oleuropein content and a sufficient anti-glycation potency can be obtained.

Fifth Condition: The Amount of Leaves Added

When the amount of leaves added is, but not limited to, 15% by weight to 35% by weight, a favorable result can be obtained in respect of the oleuropein content and the anti-glycation potency.

By satisfying at least one or any combination of two or more of the first condition to the fifth condition above, or all of them, an olive leaf extract can be produced that has a sufficiently high total polyphenol content, a sufficiently high oleuropein content, and a sufficiently high anti-glycation potency.

Example 1

Table 8 lists the total polyphenol content, the oleuropein content, and the anti-glycation potency in the olive leaf extract extracted under the first to fifth conditions above. More specifically, on the premise that the olive leaves ground after drying are used, the cultivar of olive leaves used was Lucca, Mission, Nevadillo Blanco, or Manzanillo, the extraction solvent was water, the extraction temperature was from 70° C. to 80° C., the extraction time was 3 hours, and the amount of leaves added was 20% by weight with respect to the extraction solvent. The total polyphenol content (mg/100 g), the oleuropein content (mg/100 g), and the anti-glycation potency (IC50) of the olive leaf extracts produced through extraction under such conditions were measured.

TABLE 8

| Optimum conditions | Total polyphenol content (mg/100 g) | Oleuropein content (mg/100 g) | Anti-glycation potency (IC50) |
| --- | --- | --- | --- |
| Mission | 670 | 73 | 43 |
| Lucca | 1360 | 1857 | 72 |
| Nevadillo Blanco | 960 | 1000 | 66 |
| Manzanillo | 1221 | 1334 | 88 |

As illustrated above, under the conditions above, for all of the four cultivars, the total polyphenol content has a high value, and the oleuropein content has a high value, especially for Lucca. All of the four cultivars exhibit high values for the anti-glycation potency. By comparison with Table 4 listing the result of measurement obtained under the basic extraction conditions, all of the total polyphenol content, the oleuropein content, and the anti-glycation potency are increased, which proves that the effect of the extraction under the extraction conditions above is extremely high.

Example 2

In Example 2, with the first to fifth conditions above as extraction conditions, the olive leaves ground after drying were mixed with red grape skin and subjected to extraction with water. The cultivar used was Mission, the extraction temperature was from 70° C. to 80° C., the extraction time was 3 hours, the amount of leaves added was 20% by weight with respect to the extraction solvent, and the amount of grape skin added was 10% by weight with respect to the extraction solvent. The result is listed in Table 9.

TABLE 9

| Mixture extraction/Water | Total polyphenol content (mg/100 g) |
| --- | --- |
| Red grape skin | 226 |
| Olive leaves | 499 |
| Red grape skin + olive leaves | 853 |

As illustrated above, the extraction of the olive leaf extract was confirmed that it contains polyphenols exceeding the sum of the theoretical value of polyphenols simply extracted from olive leaves and the theoretical value of polyphenols extracted from the skin of grapes as fruit.

Example 3

In Example 3, with the first to fifth conditions above as extraction conditions, the cultivar used was changed to Lucca, and the olive leaves ground after drying were mixed with the skin of red grapes and subjected to extraction with water. The extraction temperature was from 70° C. to 80° C., the extraction time was 3 hours, the amount of leaves added was 20% by weight with respect to the extraction solvent, and the amount of grape skin added was 10% by weight with respect to the extraction solvent. The result is listed in Table 10.

TABLE 10

| Mixture extraction/Water | Total polyphenol content (mg/100 g) | Oleuropein content (mg/100 g) |
|---|---|---|
| Olive leaves | 1199 | 1888 |
| Red grape skin + olive leaves | 1648 | 2765 |

Also in this case, the extraction of the olive leaf extract was confirmed that it contains polyphenols exceeding the sum of the theoretical value of polyphenols simply extracted from olive leaves and the theoretical value of polyphenols extracted from the skin of grapes as fruit.

Example 4

In Example 4, with the first to fifth conditions above as extraction conditions, the cultivar used was changed to Lucca, and the olive leaves ground after drying were mixed with the skin of red grapes and subjected to extraction with 30% 1,3-butylene glycol. The extraction temperature was from 70° C. to 80° C., the extraction time was 3 hours, the amount of leaves added was 20% by weight with respect to the extraction solvent, and the amount of grape skin added was 10% by weight with respect to the extraction solvent. The result is listed in Table 11.

TABLE 11

| Mixture extraction/30% BG | Total polyphenol content (mg/100 g) |
|---|---|
| Red grape skin | 465 |
| Olive leaves | 1106 |
| Red grape skin + olive leaves | 3235 |

Also in this case, the extraction of the olive leaf extract was confirmed that it contains polyphenols exceeding the sum of the theoretical value of polyphenols simply extracted from olive leaves and the theoretical value of polyphenols extracted from the skin of grapes as fruit.

Example 5

In Example 5, the antioxidant potency of the olive leaf extract obtained from olive leaves alone and that of the olive leaf extract (mixture extract) obtained from the mixture of olive leaves and red grape skin were measured. Each of the ° RAC value (μmol TE/g) obtained through the measurement is listed in Table 12.

TABLE 12

| | ORAC value (μmol TE/g) |
|---|---|
| Olive leaf extract | 98 |
| Mixture extract of red grape skin and olive leaf | 140 |

As illustrated above, it was confirmed that the mixture extract of red grape skin and olive leaves has an antioxidant potency significantly higher than the olive leaf extract.

Although the embodiment of the present invention has been described above, the present invention is not limited thereto and is susceptible to various modifications and changes without departing from the spirit of the invention.

INDUSTRIAL APPLICABILITY

The present invention can be used in production of an olive leaf extract containing a high concentration of oleuropein, and medicines, foods, and cosmetics containing the same.

The invention claimed is:

1. A method of producing an olive leaf extract, the method comprising:
a first step of grinding dried olive leaves; and
a second step of mixing grapes with the ground olive leaves and then extracting an olive leaf extract using an extraction solvent, wherein
in the second step, the extraction solvent is water, alcohol, or a combination thereof, and extraction is performed at 70° C. or higher.

2. The method of producing an olive leaf extract according to claim 1, wherein the amount of the olive leaves added with respect to the extraction solvent is not less than 15% by weight and not more than 35% by weight.

3. The method of producing an olive leaf extract according to claim 1, wherein a cultivar of the olive leaves is at least one selected from the group consisting of Lucca, Mission, Nevadillo Blanco, and Manzanillo.

4. The method of producing an olive leaf extract according to claim 2 wherein a cultivar of the olive leaves is at least one selected from the group consisting of Lucca, Mission, Nevadillo Blanco, and Manzanillo.

5. The method of producing an olive leaf extract according to claim 1, wherein the extracting is carried out for at least one hour.

6. The method of producing an olive leaf extract according to claim 3, wherein a cultivar of the olive leaves is at least Lucca.

7. The method of producing an olive leaf extract according to claim 1, wherein the grapes are in the form of red grape skin.

* * * * *